United States Patent [19]

Etheredge, III et al.

[11] Patent Number: 5,133,477
[45] Date of Patent: Jul. 28, 1992

[54] PACKAGING FOR ADHESIVE DRESSING

[75] Inventors: Robert W. Etheredge, III, Natick; John C. Charkoudian, Carlisle, both of Mass.

[73] Assignee: The Kendall Company, Lexington, Mass.

[21] Appl. No.: 459,175

[22] Filed: Dec. 29, 1989

[51] Int. Cl.⁵ ............................................. B65H 5/28
[52] U.S. Cl. ................................... 221/25; 206/441; 206/460; 206/470
[58] Field of Search .................. 221/70, 73, 25; 206/441, 440, 460, 467, 470, 390, 389, 343, 275, 271, 263, 262, 261

[56] References Cited

U.S. PATENT DOCUMENTS

| 3,347,361 | 10/1967 | Lindeke | 206/460 X |
| 3,835,992 | 9/1974 | Adams, IV | 221/70 X |
| 4,182,449 | 1/1980 | Kozlow | 206/441 |
| 4,574,951 | 3/1986 | Weaver | 206/470 X |
| 4,666,040 | 5/1987 | Murata | 206/441 |

FOREIGN PATENT DOCUMENTS

| 253560 | 3/1963 | Australia | 206/470 |
| 1027844 | 4/1958 | Fed. Rep. of Germany | 206/441 |

Primary Examiner—David H. Bollinger
Attorney, Agent, or Firm—M. Maus

[57] ABSTRACT

A dispenser for plurality of finger bandages comprising: (a) a release liner treated base sheet; (b) a plurality of individual wound dressings each comprising: (i) a backing; (ii) an adhesive layer on one surface thereof; (iii) a pad adapted for covering a wound disposed on the adhesive surface between opposed ends of the backing; (iv) a release liner covering one exposed adhesive surface and the pad, the other exposed adhesive surface is releasably attached to the release liner treated base sheets.

2 Claims, 2 Drawing Sheets

PACKAGING FOR ADHESIVE DRESSING

BACKGROUND OF THE INVENTION

The present invention relates in general to a novel packaging and dispensing system for finger bandages and in particular to packaging systems for a plurality of finger bandages.

Commercially available finger bandages are individually wrapped. The most widely used packaging means comprises an outer wrapper which must be torn open to obtain a finger bandage enclosed therein. Such finger bandages, typically consist of a backing, on one side of which is a pressure sensitive adhesive coating on which a pad is centrally positioned. Both adhesive coated areas are covered with individual release liners.

While the aforementioned prior art packaging does accomplish a sterile enclosure it does have disadvantages.

The primary disadvantages can collectively be attributed to awkwardness and/or difficulty in application. In order to apply the prior art bandage one first needs to remove the bandage from its outer wrapping, e.g. by pulling apart the unattached ends of the outer package; then individually peel off each release liner one at a time. Notably, when one release liner is removed, one needs to hold on to the adhesive surface on one side while removing the other release liner or risk contamination of the pad prior to application to a wound. Depending on the aggressiveness of the adhesive holding on to the adhesive surface can be quite cumbersome. For one, maneuvering the bandage into a position over the wound can lead to the adhesive surface sticking to itself, making application at a minimum uncomfortable if not impossible and often amounting to discarding of the entire bandage and starting anew.

The aforementioned disadvantage in application is not only cumbersome and time consuming but a delay in application has the more deleterious effect of increasing the exposure of a wound to environmental contaminants.

An additional disadvantage of the prior art highlighted by present day societal concerns, is the economic and ecological waste encountered with 2 throw away release liners.

Still a further disadvantage of the prior art particularly deleterious when considering the application of finger bandages to wounds, is evidenced in the difficulty encountered with opening said bandages. As previously described, the bandage is opened by pulling the outer packaging in opposite directions. Given the circumstances necessitating a bandage, opening is usually done with urgency. Thus the unsecured enclosed bandage easily falls out of its enclosure if not held in a perfect horizontal position. This scenario again leads to contamination and inapplicability to wounds resulting in economic waste.

Still a further disadvantage lies not in the particular packaging but in the very fact that each bandage is individually wrapped.

It is also known in the art to provide a box of finger bandages comprising a roll of individually wrapped bandages, which roll is perforated horizontally between finger bandages so as to dilineate individually wrapped bandages. The customer uses such dispensing means by tearing along the perforated line and opening each individual wrapper in the aforementioned manner, thereby encountering the same disadvantages as mentioned before.

Illustrative of prior art bandages is U.S. Pat. No. 4,182,449 issued to Kozlow, which discloses "an adhesive bandage and package is provided wherein the package portion of the bandage serves as means by which the bandage may be applied to the wound without affecting sterility. More precisely, the adhesive bandage, having a backing, and a pad with a facing, and is partially covered by a first covering material covering just the pad and one adhesive coated area and serves as means to apply the bandage. The partially covered adhesive bandage is covered by a second suitable covering material that is heat, pressure, or ultrasonic sealed on the four sides parallel to the edges of the cover. One portion of the cover extends beyond the seal lines and serves as means for opening and applying the bandage."

The present invention obviates the disadvantages of and distinguishes over the prior art in an elegant and novel manner, as will be seen in the following description.

SUMMARY OF THE INVENTION

The disadvantages of the prior art are overcome by the present invention by providing a novel packaging and dispensing system for finger bandages wherein a plurality of finger bandages are contained on a common release-coated support sheet. Specifically, one adhesive surface is adhered to the common release-coated surface, the other having a release sheet secured thereto so that it is unattached from the common surface, whereby the free end may be grabbed to dispense the bandage.

DETAILED DESCRIPTION OF THE INVENTION - FIG. 1

Figure 1:
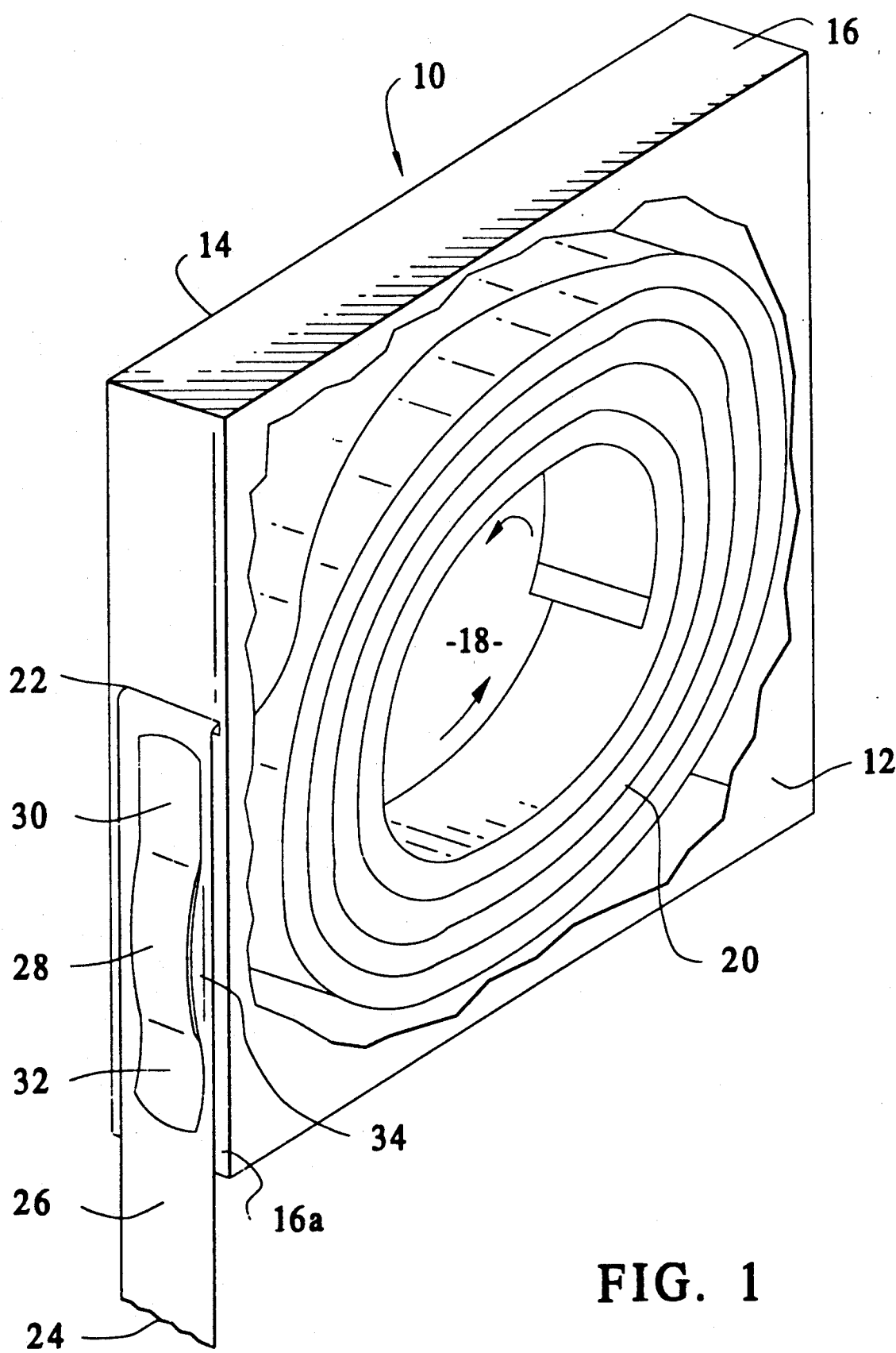
FIG. 1 is a perspective view of one preferred embodiment of the invention comprising an elongated strip.

FIG. 1 illustrates one preferred embodiment of the invention wherein a common support is employed for the individual bandages. As shown therein, a package for dispensing finger bandages is provided comprising an outer container having a front(12), back(14) and edge walls(16) defining a chamber(18) in which an elongated strip of bandages(20) may be contained, as described hereinafter. One edge wall(16a) is provided with a slit or opening(22) through which the leading end(24) of the elongated strip extends.

The elongated strip(20) consists of a continuous carrier strip(26) having a release coating on at least one surface thereof. The individual bandages(28) are positioned in spaced relationship on this strip with the trailing adhesive end(30) of each bandage secured to the release coating of carrier strip(26). The leading adhesive end(32) of the bandages, i.e. the adhesive on the side of the gauze pad first removed from the package contains a release liner(34) so that the leading end is not secured to the carrier strip.

As shown, the elongated strip is provided within the package in roll form. Where found desirable or expedient to do so, it may be disposed on a core or roll (not shown) to facilitate rotation within the package.

In operations, the leading end(24) of the carrier strip outside the package is pulled to reveal the first finger bandage, the leading end of which is not secured to the carrier strip and thus may be grabbed to release the bandage.

Figure 2:
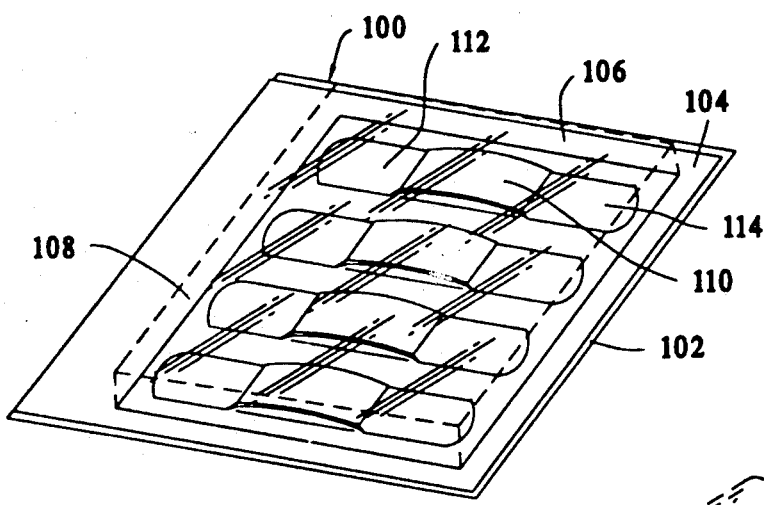
FIG. 2 is a perspective view of another embodiment of the invention comprising a sheet.
Figure 3:
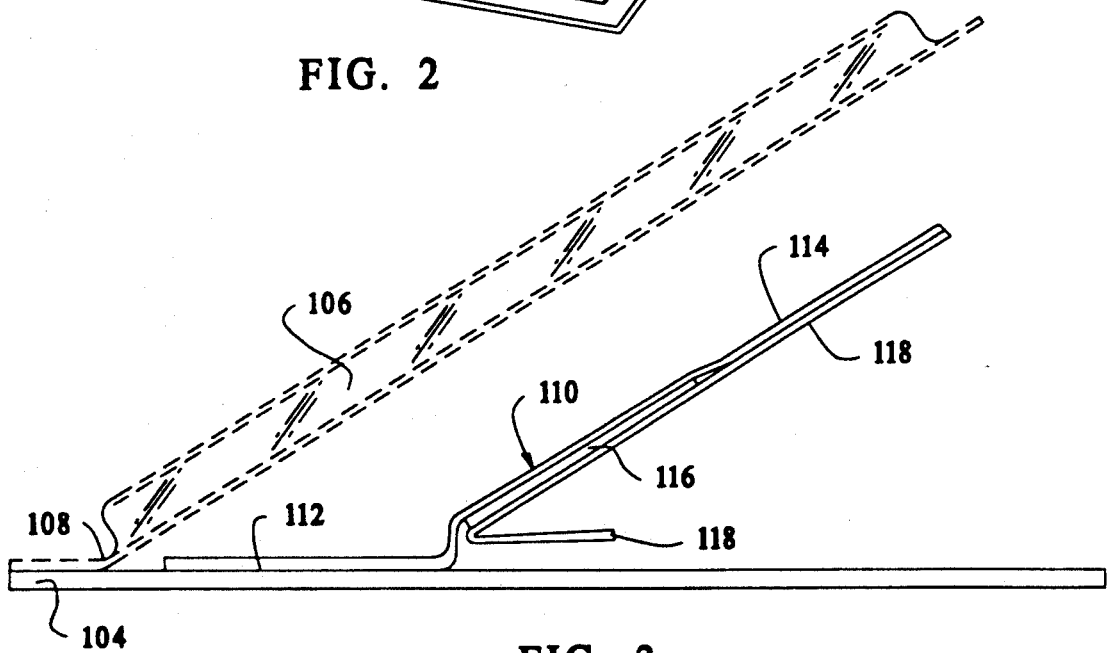
FIG. 3 is a partially schematic side elevational view of the embodiment of FIG. 2 illustrating the manner of removing a bandage from its container.

In another preferred embodiment shown in FIG. 2, the package 100, is shown to comprise a base sheet 102, having a release coating 104, on the upper surface thereof. A raised lid 106, is pivotally hinged along one edge 108 to the base sheet so as to be movable between an open and a closed position for access to a plurality of finger bandages 110 housed therein. While for purposes of illustration the package 100, is shown to contain a single row of four finger bandages 110, it will be appreciated that the dimensions of the package may be modified so as to contain more or less finger bandages than is shown in the drawings. As is best shown in FIG. 3 each finger bandage 110 in known manner contains adhesive tapes 112 and 114 on opposed sides of a centrally disposed pad 116. One of the opposed adhesive surfaces is secured to the release coated base sheet and the other adhesive surface is protected by a release liner so that it is unattached from the base sheet 104. With reference to FIG. 3 adhesive surface 112, is shown to be releasably secured to base sheet 104, while adhesive surface 114, is provided with a release sheet 118, which covers both adhesive surface 114 and pad 116.

In operation lid 106 is simply pivoted to the open position (as shown in FIG. 3) so that one or more finger bandages may be grabbed by the detached end and stripped from the base sheet 104. Upon removal of release sheet 118, the finger bandage may then be applied on the wound.

By way of recapitulation, the present invention advantageously provides for a novel dispensing means for a plurality of finger bandages, which obviates one release liner thereby facilitating ease of application and diminishing economic and ecological waste. More specifically, the prior art difficulties encountered in application, are eliminated by providing for a mechanism that only requires one free hand, so that the other hand if injured can be held still or if uninjured can attend to the wound on another body part.

We claim:

1. A dispenser for plurality of finger bandages comprising
   a. a release liner treated base sheet;
   b. a plurality of individual wound dressings each comprising
      (i) a backing;
      (ii) an adhesive layer on one surface thereof;
      (iii) a pad adapted for covering a wound disposed on the adhesive surface between opposed ends of said backing;
      (iv) a release liner covering one exposed adhesive surface and the pad, the other exposed adhesive surface is releasably attached to said release liner treated base sheets; and
   c. a lid which covers all of said individual wound dressings and is pivotally hinged to said base sheet so as to be movable between an open and closed position.

2. The dispenser for a plurality of finger bandages as described in claim 1, wherein the cover consists of clear plastic.

* * * * *